United States Patent
Donoho

(10) Patent No.: US 8,292,863 B2
(45) Date of Patent: Oct. 23, 2012

(54) DISPOSABLE DIAPER WITH POUCHES

(76) Inventor: Christopher D. Donoho, San Diego, CA (US)

( * ) Notice: Subject to any disclaimer, the term of this patent is extended or adjusted under 35 U.S.C. 154(b) by 422 days.

(21) Appl. No.: 12/582,836

(22) Filed: Oct. 21, 2009

(65) Prior Publication Data

US 2011/0092939 A1 Apr. 21, 2011

(51) Int. Cl.
*A61F 13/15* (2006.01)

(52) U.S. Cl. ......... 604/385.06; 604/385.02; 604/385.01; 604/385.19; 604/385.13

(58) Field of Classification Search ............. 604/385.02, 604/385.06, 385.01, 385.19, 385.13
See application file for complete search history.

(56) References Cited

U.S. PATENT DOCUMENTS

| | | | |
|---|---|---|---|
| 3,877,432 A | 4/1975 | Gellert |
| 3,956,224 A | 5/1976 | Chu |
| 3,963,805 A | 6/1976 | Chu |
| 3,966,679 A | 6/1976 | Gross |
| 3,971,852 A | 7/1976 | Brenner et al. |
| 3,980,663 A | 9/1976 | Gross |
| 3,993,616 A | 11/1976 | Gross |
| 4,008,189 A | 2/1977 | Van Leuwen et al. |
| 4,008,353 A | 2/1977 | Gross |
| 4,017,653 A | 4/1977 | Gross |
| 4,018,226 A | 4/1977 | Korgemets |
| 4,018,951 A | 4/1977 | Gross |
| 4,041,020 A | 8/1977 | Gross |
| 4,041,228 A | 8/1977 | Gross |
| 4,041,231 A | 8/1977 | Gross |
| 4,042,180 A | 8/1977 | Nordgren |
| 4,056,502 A | 11/1977 | Gross |
| 4,056,919 A | 11/1977 | Hirsch |
| 4,057,521 A | 11/1977 | Gross |
| 4,061,846 A | 12/1977 | Gross |
| 4,065,179 A | 12/1977 | Takasaki |
| 4,071,650 A | 1/1978 | Gross |
| 4,076,673 A | 2/1978 | Burkholder |
| 4,076,928 A | 2/1978 | Gross |
| 4,079,029 A | 3/1978 | Gross |
| 4,085,753 A | 4/1978 | Gellert |
| 4,132,695 A | 1/1979 | Burkholder |
| 4,133,056 A | 1/1979 | Crump, Jr. |
| 4,133,063 A | 1/1979 | Jones-Steele |
| 4,141,193 A | 2/1979 | Joa |
| 4,154,898 A | 5/1979 | Burkholder, Jr. |
| 4,155,693 A | 5/1979 | Raley |
| 4,157,237 A | 6/1979 | Raley |
| 4,169,121 A | 9/1979 | Pietsch et al. |
| 4,252,236 A | 2/1981 | Roccaforte |
| 4,252,279 A | 2/1981 | Johansson et al. |
| 4,252,516 A | 2/1981 | Raley et al. |
| D260,453 S | 9/1981 | Carlson |
| 4,289,513 A | 9/1981 | Brownhill et al. |
| 4,293,609 A | 10/1981 | Erickson |
| 4,310,593 A | 1/1982 | Gross |
| 4,317,792 A | 3/1982 | Raley et al. |

(Continued)

*Primary Examiner* — Lynne Anderson
*Assistant Examiner* — Bradley Philips
(74) *Attorney, Agent, or Firm* — John L. Rogitz

(57) ABSTRACT

A disposable diaper has a front pouch with a wet wipe inside and a rear pouch with a closable open end. When the diaper has been soiled the wet wipe can be removed from the front pouch and used to clean the baby and then the diaper, once removed from the baby, can be inverted into the rear pouch, which inverts inside out with the soiled diaper inside. A closure can be used to close the open end of the now-inverted rear pouch to contain the soiled diaper inside.

14 Claims, 2 Drawing Sheets

U.S. PATENT DOCUMENTS

| | | |
|---|---|---|
| 4,338,371 A | 7/1982 | Dawn et al. |
| 4,343,848 A | 8/1982 | Leonard, Jr. |
| 4,353,762 A | 10/1982 | Bouda |
| 4,356,818 A | 11/1982 | Macias et al. |
| 4,360,632 A | 11/1982 | Pinschmidt, Jr. et al. |
| 4,379,103 A | 4/1983 | Doerfling |
| 4,411,660 A | 10/1983 | Dawn et al. |
| 4,413,109 A | 11/1983 | Haas |
| 4,416,727 A | 11/1983 | Elton et al. |
| 4,447,570 A | 5/1984 | Cook et al. |
| 4,449,978 A | 5/1984 | Iacoviello |
| 4,466,146 A | 8/1984 | Regan |
| 4,481,250 A | 11/1984 | Cook et al. |
| 4,483,895 A | 11/1984 | Deaver |
| 4,486,374 A | 12/1984 | Stelzer |
| 4,493,713 A | 1/1985 | Izzo |
| 4,500,316 A | 2/1985 | Damico |
| 4,500,585 A | 2/1985 | Erickson |
| 4,518,643 A | 5/1985 | Francis |
| 4,519,798 A | 5/1985 | Dinius |
| 4,524,887 A | 6/1985 | Cocks |
| 4,530,862 A | 7/1985 | Kerzel |
| 4,541,794 A | 9/1985 | Raley et al. |
| 4,547,243 A | 10/1985 | Brody |
| 4,573,987 A | 3/1986 | Lamb, Jr. |
| 4,587,319 A | 5/1986 | Tournier |
| 4,589,166 A | 5/1986 | Holvoet |
| 4,601,717 A | 7/1986 | Blevins |
| 4,604,096 A | 8/1986 | Dean |
| 4,605,401 A | 8/1986 | Chmelir et al. |
| 4,624,793 A | 11/1986 | Phifer et al. |
| 4,636,161 A | 1/1987 | Raley et al. |
| 4,637,634 A | 1/1987 | Troy et al. |
| 4,642,150 A | 2/1987 | Stemmler |
| 4,642,151 A | 2/1987 | Coenen |
| 4,644,623 A | 2/1987 | Raley et al. |
| 4,674,135 A | 6/1987 | Greene |
| 4,674,966 A | 6/1987 | Johnson et al. |
| 4,681,793 A | 7/1987 | Linman et al. |
| 4,701,239 A | 10/1987 | Craig |
| 4,711,683 A | 12/1987 | Merkatoris |
| 4,725,473 A | 2/1988 | Van Gompel et al. |
| 4,729,516 A | 3/1988 | Williams, Jr. |
| 4,731,070 A | 3/1988 | Koci |
| 4,731,407 A | 3/1988 | Benim et al. |
| 4,738,675 A | 4/1988 | Buckley et al. |
| 4,738,678 A | 4/1988 | Paulis |
| 4,743,240 A * | 5/1988 | Powell ............... 604/385.13 |
| 4,751,132 A | 6/1988 | Benim et al. |
| 4,764,234 A | 8/1988 | Smits et al. |
| 4,764,242 A | 8/1988 | Gressick et al. |
| 4,766,173 A | 8/1988 | Bailey et al. |
| 4,769,023 A | 9/1988 | Goebel et al. |
| 4,776,911 A | 10/1988 | Uda et al. |
| 4,778,458 A | 10/1988 | Gronostajski |
| 4,790,840 A | 12/1988 | Cortina |
| 4,795,451 A | 1/1989 | Buckley |
| 4,808,175 A | 2/1989 | Hansen |
| 4,809,375 A | 3/1989 | Bull |
| 4,833,195 A | 5/1989 | Adur et al. |
| 4,833,222 A | 5/1989 | Siddall et al. |
| 4,838,886 A | 6/1989 | Kent |
| 4,840,695 A | 6/1989 | Benim |
| 4,842,877 A | 6/1989 | Tyson |
| 4,846,587 A | 7/1989 | Hull |
| 4,848,989 A | 7/1989 | Maeda |
| 4,865,097 A | 9/1989 | Allen |
| 4,867,575 A | 9/1989 | Wood |
| 4,877,856 A | 10/1989 | Hall et al. |
| 4,885,204 A | 12/1989 | Bither et al. |
| 4,885,844 A | 12/1989 | Chun |
| 4,889,284 A | 12/1989 | Spector |
| 4,891,249 A | 1/1990 | McIntyre |
| 4,892,534 A | 1/1990 | Datta et al. |
| 4,892,535 A | 1/1990 | Bjornberg et al. |
| 4,895,742 A | 1/1990 | Schaub et al. |
| 4,902,559 A | 2/1990 | Eschwey et al. |
| 4,904,249 A | 2/1990 | Miller et al. |
| 4,904,252 A | 2/1990 | Fitzgerald |
| 4,908,089 A | 3/1990 | Uda et al. |
| 4,911,563 A | 3/1990 | Ciani |
| 4,923,455 A | 5/1990 | Dean |
| 4,924,084 A | 5/1990 | Lask et al. |
| 4,931,052 A | 6/1990 | Feldman |
| 4,934,535 A | 6/1990 | Muckenfuhs et al. |
| 4,935,260 A | 6/1990 | Shlenker |
| 4,965,896 A | 10/1990 | Berger et al. |
| 4,966,286 A | 10/1990 | Muckenfuhs |
| 4,982,688 A | 1/1991 | Rothen |
| 4,988,332 A | 1/1991 | Mattle |
| 4,996,091 A | 2/1991 | McIntyre |
| 5,002,814 A | 3/1991 | Knack et al. |
| 5,004,466 A | 4/1991 | Uda et al. |
| 5,010,617 A | 4/1991 | Nelson |
| 5,022,216 A | 6/1991 | Muckenfuhs et al. |
| 5,023,097 A | 6/1991 | Tyson |
| 5,042,227 A | 8/1991 | Merry |
| 5,045,341 A | 9/1991 | Shlenker |
| 5,046,272 A | 9/1991 | Vogt et al. |
| 5,054,619 A | 10/1991 | Muckenfuhs |
| 5,057,361 A | 10/1991 | Sayovitz et al. |
| 5,060,849 A | 10/1991 | King |
| 5,068,009 A | 11/1991 | Jokinen et al. |
| 5,074,853 A | 12/1991 | Bryant |
| 5,075,344 A | 12/1991 | Johnson |
| 5,075,938 A | 12/1991 | Hutchinson |
| 5,077,870 A | 1/1992 | Melbye et al. |
| 5,091,240 A | 2/1992 | Kajander et al. |
| 5,096,424 A | 3/1992 | Carlberg |
| 5,112,326 A | 5/1992 | Quadrini |
| 5,112,391 A | 5/1992 | Owen et al. |
| 5,113,553 A | 5/1992 | Hutchinson |
| 5,118,376 A | 6/1992 | Pigneul et al. |
| 5,126,201 A | 6/1992 | Shiba et al. |
| 5,127,911 A | 7/1992 | Baharav |
| 5,139,861 A | 8/1992 | Williams et al. |
| 5,147,532 A | 9/1992 | Leek, Jr. |
| 5,149,332 A | 9/1992 | Walton et al. |
| 5,150,561 A | 9/1992 | Muckenfuhs |
| 5,152,440 A | 10/1992 | Chao |
| 5,171,236 A | 12/1992 | Dreier et al. |
| 5,172,435 A | 12/1992 | Griffin et al. |
| 5,172,629 A | 12/1992 | Merry |
| 5,183,872 A | 2/1993 | Heidel et al. |
| 5,188,624 A | 2/1993 | Young, Sr. et al. |
| 5,195,765 A | 3/1993 | Lacey, Jr. |
| 5,196,244 A | 3/1993 | Beck |
| 5,199,139 A | 4/1993 | Hutchinson |
| 5,219,229 A | 6/1993 | Sengewald |
| 5,230,736 A | 7/1993 | Schnodewind |
| 5,232,777 A | 8/1993 | Sipinen et al. |
| 5,243,708 A | 9/1993 | Vanuch |
| 5,243,724 A | 9/1993 | Barnes |
| 5,246,431 A | 9/1993 | Minetola et al. |
| 5,246,596 A | 9/1993 | Baldwin, Jr. et al. |
| 5,262,064 A | 11/1993 | El-Shall |
| 5,266,928 A | 11/1993 | Johnson |
| 5,269,776 A | 12/1993 | Lancaster et al. |
| 5,275,592 A | 1/1994 | Grizzaffi |
| 5,275,760 A | 1/1994 | Johnson |
| 5,290,104 A | 3/1994 | Sengewald |
| 5,290,626 A | 3/1994 | Nishioi et al. |
| 5,292,347 A | 3/1994 | Pompei |
| 5,295,986 A | 3/1994 | Zehner et al. |
| 5,300,053 A | 4/1994 | Genaro |
| 5,300,104 A | 4/1994 | Gaudreault et al. |
| 5,302,443 A | 4/1994 | Manning et al. |
| 5,314,119 A | 5/1994 | Watt |
| 5,318,553 A | 6/1994 | Weeks et al. |
| 5,324,279 A | 6/1994 | Lancaster et al. |
| 5,325,543 A | 7/1994 | Allen |
| 5,328,450 A | 7/1994 | Smith et al. |
| 5,336,552 A | 8/1994 | Srack et al. |
| 5,337,934 A | 8/1994 | Johnson et al. |
| 5,342,344 A | 8/1994 | Lancaster et al. |
| 5,344,691 A | 9/1994 | Hanschen et al. |
| 5,346,708 A | 9/1994 | Carson |

| Patent No. | Date | Inventor |
|---|---|---|
| 5,360,504 A | 11/1994 | Fell et al. |
| 5,366,453 A | 11/1994 | Zehner et al. |
| 5,366,591 A | 11/1994 | Jewell |
| 5,370,715 A | 12/1994 | Kortzeborn et al. |
| 5,376,430 A | 12/1994 | Swenson et al. |
| 5,380,094 A | 1/1995 | Schmidt et al. |
| 5,382,400 A | 1/1995 | Pike et al. |
| 5,385,983 A | 1/1995 | Graham |
| 5,389,384 A | 2/1995 | Jooste |
| 5,399,177 A | 3/1995 | Blaney et al. |
| 5,405,682 A | 4/1995 | Shawyer et al. |
| 5,413,747 A | 5/1995 | Akers et al. |
| 5,415,926 A | 5/1995 | Leighton et al. |
| 5,416,160 A | 5/1995 | Johnson |
| 5,418,045 A | 5/1995 | Pike et al. |
| 5,422,172 A | 6/1995 | Wu |
| 5,422,178 A | 6/1995 | Swenson et al. |
| 5,425,987 A | 6/1995 | Shawver et al. |
| 5,431,644 A | 7/1995 | Sipinen et al. |
| 5,439,154 A | 8/1995 | Delligatti |
| 5,447,727 A | 9/1995 | Graham |
| 5,449,464 A | 9/1995 | El-Shall |
| 5,462,708 A | 10/1995 | Swenson et al. |
| 5,466,731 A | 11/1995 | Akers et al. |
| 5,467,765 A | 11/1995 | Maturaporn |
| 5,468,428 A | 11/1995 | Hanschen et al. |
| 5,469,145 A | 11/1995 | Johnson |
| 5,476,456 A | 12/1995 | Rankin et al. |
| D366,315 S | 1/1996 | Oranday |
| 5,482,772 A | 1/1996 | Srack et al. |
| 5,489,282 A | 2/1996 | Zehner et al. |
| 5,500,063 A | 3/1996 | Jessup |
| 5,501,679 A | 3/1996 | Krueger et al. |
| 5,506,324 A | 4/1996 | Gartner et al. |
| 5,512,358 A | 4/1996 | Shaever et al. |
| 5,514,067 A | 5/1996 | Schmidt et al. |
| 5,514,120 A | 5/1996 | Johnston et al. |
| 5,527,302 A | 6/1996 | Endres et al. |
| 5,527,305 A | 6/1996 | Goulait et al. |
| 5,531,732 A | 7/1996 | Wood |
| 5,540,987 A | 7/1996 | Mudge et al. |
| 5,540,992 A | 7/1996 | Marcher et al. |
| 5,543,157 A | 8/1996 | Trinh et al. |
| 5,545,158 A | 8/1996 | Jessup |
| 5,545,159 A | 8/1996 | Lancaster et al. |
| 5,549,591 A | 8/1996 | Landvogt |
| 5,552,378 A | 9/1996 | Trinh et al. |
| 5,556,976 A | 9/1996 | Jewell |
| 5,571,782 A | 11/1996 | Trinh et al. |
| 5,575,782 A | 11/1996 | Hasse et al. |
| 5,576,037 A | 11/1996 | Moore, Jr. et al. |
| 5,580,851 A | 12/1996 | Trinh et al. |
| 5,591,151 A | 1/1997 | Hasse et al. |
| 5,599,336 A | 2/1997 | Plischke |
| 5,601,542 A | 2/1997 | Melius et al. |
| 5,601,545 A | 2/1997 | Glaug et al. |
| 5,601,547 A | 2/1997 | Kato et al. |
| 5,601,921 A | 2/1997 | Eriksson |
| 5,607,635 A | 3/1997 | Melbye et al. |
| 5,609,619 A | 3/1997 | Pompei |
| 5,615,433 A | 4/1997 | Martin |
| 5,629,377 A | 5/1997 | Burgert et al. |
| 5,633,316 A | 5/1997 | Gartner et al. |
| 5,635,238 A | 6/1997 | Trinh et al. |
| 5,641,562 A | 6/1997 | Larson et al. |
| 5,657,917 A | 8/1997 | Johnson et al. |
| 5,660,845 A | 8/1997 | Trinh et al. |
| 5,669,900 A | 9/1997 | Bullwinkel et al. |
| 5,669,996 A | 9/1997 | Jessup |
| 5,677,028 A | 10/1997 | Ravella |
| 5,679,302 A | 10/1997 | Miller et al. |
| 5,681,894 A | 10/1997 | Williams et al. |
| D386,582 S | 11/1997 | Levine |
| 5,683,376 A | 11/1997 | Kato et al. |
| 5,685,873 A | 11/1997 | Bruemmer |
| 5,691,034 A | 11/1997 | Krueger et al. |
| 5,692,766 A | 12/1997 | Wheeler |
| 5,698,322 A | 12/1997 | Tsai et al. |
| 5,701,622 A | 12/1997 | Biggie et al. |
| 5,707,707 A | 1/1998 | Burnes et al. |
| 5,709,747 A | 1/1998 | Goldwasser |
| 5,711,832 A | 1/1998 | Glaug et al. |
| 5,728,446 A | 3/1998 | Johnston et al. |
| 5,740,556 A | 4/1998 | Brown |
| 5,744,150 A | 4/1998 | Cercone |
| 5,752,946 A | 5/1998 | Boberg et al. |
| 5,754,999 A | 5/1998 | Helmsderfer |
| 5,765,487 A | 6/1998 | Neff |
| 5,767,189 A | 6/1998 | Palmer, Jr. |
| 5,769,993 A | 6/1998 | Baldauf |
| 5,770,308 A | 6/1998 | Suzuki et al. |
| 5,772,649 A | 6/1998 | Siudzinski |
| 5,772,813 A | 6/1998 | Bitowft et al. |
| 5,772,825 A | 6/1998 | Schmitz |
| 5,773,564 A | 6/1998 | Sikes |
| 5,796,345 A | 8/1998 | Leventis et al. |
| 5,799,909 A | 9/1998 | Ziegler |
| 5,801,116 A | 9/1998 | Cottrell et al. |
| 5,802,647 A | 9/1998 | Helmsderfer |
| 5,807,368 A | 9/1998 | Helmer |
| 5,813,558 A | 9/1998 | Burke |
| 5,817,713 A | 10/1998 | Pappas et al. |
| 5,824,246 A | 10/1998 | Reetz |
| 5,827,443 A | 10/1998 | Kita et al. |
| 5,830,202 A | 11/1998 | Bogdanski et al. |
| 5,838,240 A | 11/1998 | Johnson |
| 5,843,554 A | 12/1998 | Katz |
| 5,845,375 A | 12/1998 | Miller et al. |
| 5,849,816 A | 12/1998 | Suskind et al. |
| 5,851,937 A | 12/1998 | Wu et al. |
| 5,860,964 A | 1/1999 | Willekens et al. |
| 5,861,074 A | 1/1999 | Wu |
| 5,864,905 A | 2/1999 | Helmsderfer |
| 5,865,926 A | 2/1999 | Wu et al. |
| 5,868,227 A | 2/1999 | Garcia |
| 5,876,840 A | 3/1999 | Ning et al. |
| 5,879,487 A | 3/1999 | Ravella |
| 5,879,604 A | 3/1999 | Melbye et al. |
| 5,885,269 A | 3/1999 | Boyer, III et al. |
| 5,885,656 A | 3/1999 | Goldwasser |
| 5,891,125 A | 4/1999 | Plumley |
| 5,895,623 A | 4/1999 | Trokhan et al. |
| 5,910,545 A | 6/1999 | Tsai et al. |
| 5,922,165 A | 7/1999 | Bitowft et al. |
| 5,928,380 A | 7/1999 | Winkler et al. |
| 5,928,665 A | 7/1999 | Cercone |
| 5,942,080 A | 8/1999 | Mortellite et al. |
| 5,951,946 A | 9/1999 | Eaton et al. |
| 5,952,088 A | 9/1999 | Tsai et al. |
| 5,960,471 A | 10/1999 | Burton |
| 5,969,026 A | 10/1999 | Mor et al. |
| 5,972,487 A | 10/1999 | Duenk et al. |
| 5,976,995 A | 11/1999 | Palmer, Jr. |
| 5,985,999 A | 11/1999 | Dominguez et al. |
| 5,986,000 A | 11/1999 | Williams et al. |
| 5,989,688 A | 11/1999 | Barge et al. |
| 5,991,943 A | 11/1999 | Morris |
| 5,998,696 A | 12/1999 | Schone |
| 6,001,935 A | 12/1999 | Palmer, Jr. |
| 6,007,524 A | 12/1999 | Schneider |
| 6,010,971 A | 1/2000 | Tsai et al. |
| 6,013,151 A | 1/2000 | Wu et al. |
| 6,018,033 A | 1/2000 | Chen et al. |
| 6,031,048 A | 2/2000 | Evans et al. |
| 6,032,310 A | 3/2000 | Helmsderfer et al. |
| 6,039,911 A | 3/2000 | Miller et al. |
| 6,040,494 A | 3/2000 | Kalentun et al. |
| 6,049,928 A | 4/2000 | Helmsderfer |
| 6,055,688 A | 5/2000 | Helmsderfer et al. |
| 6,059,924 A | 5/2000 | Hoskins |
| 6,060,637 A | 5/2000 | Bitowft et al. |
| 6,061,840 A | 5/2000 | Alligator |
| 6,063,959 A | 5/2000 | Lehnert et al. |
| 6,079,562 A | 6/2000 | Bauer et al. |
| 6,085,579 A | 7/2000 | Herrlein |
| 6,092,237 A | 7/2000 | Baldwin |
| 6,093,474 A | 7/2000 | Sironi |
| 6,093,496 A | 7/2000 | Dominguez et al. |

| | | | |
|---|---|---|---|
| 6,096,420 A | 8/2000 | Wilhoit et al. | |
| 6,107,537 A | 8/2000 | Elder et al. | |
| 6,107,539 A | 8/2000 | Palumbo et al. | |
| 6,110,849 A | 8/2000 | Tsai et al. | |
| 6,127,480 A | 10/2000 | Dominguez et al. | |
| 6,132,840 A | 10/2000 | Lee | |
| 6,135,987 A | 10/2000 | Tsai et al. | |
| 6,146,574 A | 11/2000 | Henkee et al. | |
| 6,146,757 A | 11/2000 | Mor et al. | |
| 6,149,637 A | 11/2000 | Allen et al. | |
| 6,153,209 A | 11/2000 | Vega et al. | |
| 6,156,818 A | 12/2000 | Corzani et al. | |
| 6,159,335 A | 12/2000 | Owens et al. | |
| 6,162,835 A | 12/2000 | Kramer et al. | |
| 6,164,442 A | 12/2000 | Stravitz | |
| 6,177,193 B1 | 1/2001 | Tsai et al. | |
| 6,178,278 B1 | 1/2001 | Keller et al. | |
| 6,183,847 B1 | 2/2001 | Goldwasser | |
| 6,190,369 B1 | 2/2001 | Palumbo et al. | |
| 6,191,055 B1 | 2/2001 | Boyer, III et al. | |
| 6,194,079 B1 | 2/2001 | Hekal | |
| 6,194,483 B1 | 2/2001 | Tsai et al. | |
| 6,197,237 B1 | 3/2001 | Tsai et al. | |
| 6,197,860 B1 | 3/2001 | Tsai et al. | |
| 6,201,068 B1 | 3/2001 | Tsai et al. | |
| 6,207,755 B1 | 3/2001 | Tsai et al. | |
| 6,211,272 B1 | 4/2001 | Shafer et al. | |
| 6,211,294 B1 | 4/2001 | Tsai et al. | |
| 6,214,147 B1 | 4/2001 | Mortellite et al. | |
| 6,218,009 B1 | 4/2001 | Tsai et al. | |
| 6,222,092 B1 | 4/2001 | Hansen et al. | |
| 6,224,961 B1 | 5/2001 | Hsueh et al. | |
| 6,225,388 B1 | 5/2001 | Tsai et al. | |
| 6,225,524 B1 | 5/2001 | Guarracino et al. | |
| 6,230,771 B1 | 5/2001 | Hellenbrand | |
| 6,232,521 B1 | 5/2001 | Bewick et al. | |
| 6,235,658 B1 | 5/2001 | Panzer et al. | |
| H1969 H | 6/2001 | Fell et al. | |
| 6,241,713 B1 | 6/2001 | Gross et al. | |
| 6,245,094 B1 | 6/2001 | Pompei | |
| 6,245,410 B1 | 6/2001 | Hahnle et al. | |
| 6,245,831 B1 | 6/2001 | Tsai et al. | |
| 6,245,961 B1 | 6/2001 | Roxendal et al. | |
| 6,251,479 B1 | 6/2001 | Groitzsch et al. | |
| 6,251,995 B1 | 6/2001 | Hesse et al. | |
| 6,253,012 B1 | 6/2001 | Keller et al. | |
| 6,254,565 B1 | 7/2001 | Williams et al. | |
| 6,261,278 B1 | 7/2001 | Chen et al. | |
| 6,261,677 B1 | 7/2001 | Tsai et al. | |
| 6,264,530 B1 | 7/2001 | Cosentino | |
| 6,265,045 B1 | 7/2001 | Mushaben | |
| 6,265,202 B1 | 7/2001 | Sherman et al. | |
| 6,268,434 B1 | 7/2001 | Tsai et al. | |
| 6,268,449 B1 | 7/2001 | Chang et al. | |
| H1978 H | 8/2001 | Freiburger et al. | |
| 6,269,720 B1 | 8/2001 | Pelagatti | |
| 6,270,845 B1 | 8/2001 | Pappas et al. | |
| 6,271,278 B1 | 8/2001 | Park et al. | |
| 6,278,037 B1 | 8/2001 | Schmidt et al. | |
| H1989 H | 9/2001 | Fell et al. | |
| 6,287,665 B1 | 9/2001 | Hammer | |
| 6,287,679 B1 | 9/2001 | Pappas et al. | |
| 6,294,710 B1 | 9/2001 | Schmidt et al. | |
| 6,295,658 B1 | 10/2001 | Jenkins | |
| 6,300,257 B1 | 10/2001 | Kirchberger et al. | |
| 6,306,121 B1 | 10/2001 | Damaghi et al. | |
| 6,306,782 B1 | 10/2001 | Tsai et al. | |
| 6,306,964 B1 | 10/2001 | Evans et al. | |
| 6,309,988 B1 | 10/2001 | Tsai et al. | |
| 6,315,864 B2 | 11/2001 | Anderson et al. | |
| 6,320,095 B1 | 11/2001 | Wall | |
| H2011 H | 1/2002 | Freiburger et al. | |
| 6,336,921 B1 | 1/2002 | Kato et al. | |
| 6,344,109 B1 | 2/2002 | Gross | |
| 6,346,125 B1 | 2/2002 | Mao | |
| 6,349,867 B1 | 2/2002 | Fernfors | |
| 6,353,148 B1 | 3/2002 | Gross | |
| 6,355,200 B1 | 3/2002 | Schmidt et al. | |
| 6,358,350 B1 | 3/2002 | Glaug et al. | |
| 6,358,493 B1 | 3/2002 | Birkel et al. |
| 6,359,079 B1 | 3/2002 | Palmer, Jr. |
| 6,359,192 B1 | 3/2002 | Schmidt et al. |
| 6,361,768 B1 | 3/2002 | Galleguillos et al. |
| 6,362,390 B1 | 3/2002 | Carlucci et al. |
| 6,368,097 B1 | 4/2002 | Miller et al. |
| 6,368,609 B1 | 4/2002 | Fontenot et al. |
| 6,372,954 B1 | 4/2002 | Johnston et al. |
| 6,375,000 B1 | 4/2002 | Weder et al. |
| 6,376,741 B1 | 4/2002 | Guarracino et al. |
| 6,388,166 B1 | 5/2002 | Herrlein et al. |
| 6,390,167 B1 | 5/2002 | Geissen et al. |
| 6,393,639 B1 | 5/2002 | Ohsner |
| 6,399,854 B1 | 6/2002 | Vartiainen |
| 6,403,857 B1 | 6/2002 | Gross et al. |
| 6,405,394 B1 | 6/2002 | Rosenberg |
| 6,410,138 B2 | 6/2002 | Mleziva et al. |
| 6,413,247 B1 | 7/2002 | Carlucci et al. |
| 6,413,249 B1 | 7/2002 | Turi et al. |
| 6,417,424 B1 | 7/2002 | Bewick et al. |
| 6,417,425 B1 | 7/2002 | Whitmore et al. |
| 6,417,427 B1 | 7/2002 | Roxendal et al. |
| 6,420,482 B1 | 7/2002 | Dominguez et al. |
| 6,429,352 B1 | 8/2002 | Herrlein et al. |
| 6,436,500 B1 | 8/2002 | Yingst et al. |
| 6,436,508 B1 | 8/2002 | Ciammaichella et al. |
| 6,436,529 B1 | 8/2002 | Deeb et al. |
| 6,437,212 B1 | 8/2002 | La Fortune |
| 6,437,213 B1 | 8/2002 | Schmidt et al. |
| 6,441,266 B1 | 8/2002 | Dyer et al. |
| 6,446,495 B1 | 9/2002 | Herrlein et al. |
| 6,447,497 B1 | 9/2002 | Olson |
| 6,448,467 B1 | 9/2002 | Herrlein et al. |
| 6,454,751 B1 | 9/2002 | Olson |
| 6,461,342 B2 | 10/2002 | Tanji et al. |
| 6,462,251 B1 | 10/2002 | Cimini et al. |
| 6,465,107 B1 | 10/2002 | Kelly |
| 6,465,532 B1 | 10/2002 | Hekal |
| 6,468,931 B1 | 10/2002 | Reeder et al. |
| 6,475,202 B1 | 11/2002 | Hirsch |
| 6,475,325 B1 | 11/2002 | Parrish et al. |
| 6,475,418 B1 | 11/2002 | Tsai et al. |
| 6,475,591 B2 | 11/2002 | Mushaben |
| 6,479,001 B1 | 11/2002 | Tsai et al. |
| 6,479,061 B2 | 11/2002 | Fontenot et al. |
| 6,482,870 B1 | 11/2002 | Hojjati et al. |
| 6,486,231 B1 | 11/2002 | Hekal |
| 6,494,244 B1 | 12/2002 | Parrish et al. |
| 6,494,873 B2 | 12/2002 | Karlsson et al. |
| 6,495,348 B1 | 12/2002 | Sherman et al. |
| 6,497,032 B2 | 12/2002 | Maxton et al. |
| 6,497,689 B1 | 12/2002 | Schmidt et al. |
| 6,497,695 B1 | 12/2002 | Bruemmer et al. |
| 6,497,696 B1 | 12/2002 | Freiburger et al. |
| 6,500,161 B1 | 12/2002 | Freiburger et al. |
| 6,500,162 B1 | 12/2002 | Freiburger et al. |
| 6,500,538 B1 | 12/2002 | Strack et al. |
| 6,503,239 B1 | 1/2003 | Bruemmer et al. |
| 6,503,854 B1 | 1/2003 | Abuto et al. |
| 6,506,695 B2 | 1/2003 | Gardner et al. |
| 6,506,960 B1 | 1/2003 | Young et al. |
| 6,506,995 B1 | 1/2003 | Fusaro, Jr. et al. |
| 6,508,799 B1 | 1/2003 | Freiburger et al. |
| 6,511,465 B1 | 1/2003 | Freiburger et al. |
| 6,511,566 B1 | 1/2003 | Wessel et al. |
| 6,514,187 B2 | 2/2003 | Coenen et al. |
| 6,514,235 B1 | 2/2003 | Freiburger et al. |
| 6,519,774 B2 | 2/2003 | Mitchell |
| 6,528,439 B1 | 3/2003 | Stokes et al. |
| 6,531,025 B1 | 3/2003 | Lender et al. |
| 6,531,027 B1 | 3/2003 | Lender et al. |
| 6,533,492 B1 | 3/2003 | Mullen |
| 6,533,898 B2 | 3/2003 | Gross |
| 6,540,731 B2 | 4/2003 | Magnusson et al. |
| 6,541,403 B1 | 4/2003 | Billarant et al. |
| 6,544,455 B1 | 4/2003 | Tsai |
| 6,545,194 B1 | 4/2003 | Schmidt et al. |
| 6,545,196 B1 | 4/2003 | Herrlein et al. |
| 6,550,960 B2 | 4/2003 | Catalfamo et al. |

| | | |
|---|---|---|
| 6,551,295 B1 | 4/2003 | Schmidt et al. |
| 6,551,430 B1 | 4/2003 | Glaug et al. |
| 6,554,816 B1 | 4/2003 | Olson |
| 6,558,602 B1 | 5/2003 | Melbye et al. |
| 6,559,353 B1 | 5/2003 | Sheridan |
| 6,562,742 B2 | 5/2003 | Dutkiewicz et al. |
| 6,563,013 B1 | 5/2003 | Murota |
| 6,569,135 B1 | 5/2003 | Mula |
| 6,569,137 B2 | 5/2003 | Suzuki et al. |
| 6,569,141 B1 | 5/2003 | Bruemmer et al. |
| 6,569,374 B1 | 5/2003 | Poulakis |
| 6,570,057 B1 | 5/2003 | Schmidt et al. |
| 6,570,059 B1 | 5/2003 | Carlucci et al. |
| 6,573,423 B1 | 6/2003 | Herrlein et al. |
| 6,575,953 B2 | 6/2003 | Olson |
| 6,579,273 B2 | 6/2003 | Dupuy |
| 6,579,457 B1 | 6/2003 | Ehrnsperger et al. |
| 6,590,040 B2 | 7/2003 | Sackmann et al. |
| 6,600,029 B1 | 7/2003 | Sherman et al. |
| 6,601,705 B2 | 8/2003 | Molina et al. |
| 6,605,173 B2 | 8/2003 | Glaug et al. |
| 6,607,515 B2 | 8/2003 | Glaug et al. |
| 6,608,017 B1 | 8/2003 | Dihora et al. |
| 6,616,648 B2 | 9/2003 | Hermansson et al. |
| 6,623,464 B2 | 9/2003 | Bewick et al. |
| 6,623,586 B2 | 9/2003 | Mortellite et al. |
| 6,624,341 B1 | 9/2003 | Depner et al. |
| 6,626,882 B2 | 9/2003 | Hjorth |
| 6,627,791 B1 | 9/2003 | Veglio et al. |
| 6,635,212 B1 | 10/2003 | Melbye et al. |
| 6,635,801 B1 | 10/2003 | Lankhof et al. |
| 6,645,188 B2 | 11/2003 | Kusibijoska et al. |
| 6,645,190 B1 | 11/2003 | Olson et al. |
| 6,646,179 B1 | 11/2003 | Melius et al. |
| 6,647,600 B1 | 11/2003 | Jost et al. |
| 6,648,862 B2 | 11/2003 | Watson |
| 6,648,871 B2 | 11/2003 | Kusibojoska et al. |
| 6,649,010 B2 | 11/2003 | Parrish et al. |
| 6,653,385 B2 | 11/2003 | Wang et al. |
| 6,656,581 B2 | 12/2003 | Wu et al. |
| 6,659,992 B1 | 12/2003 | Schmidt et al. |
| 6,660,211 B2 | 12/2003 | Topolkaraev et al. |
| 6,660,902 B2 | 12/2003 | Widlund et al. |
| 6,664,439 B1 | 12/2003 | Arndt et al. |
| 6,669,678 B2 | 12/2003 | Hermansson et al. |
| 6,673,057 B1 | 1/2004 | Ehrnsperger et al. |
| 6,673,297 B2 | 1/2004 | Mushaben |
| 6,676,648 B2 | 1/2004 | Bruemmer Prestley et al. |
| 6,679,754 B2 | 1/2004 | Li et al. |
| 6,680,265 B1 | 1/2004 | Smith et al. |
| 6,683,229 B1 | 1/2004 | Ehrnsperger et al. |
| 6,685,686 B2 | 2/2004 | Hermansson et al. |
| 6,686,512 B2 | 2/2004 | Herrlein et al. |
| 6,696,002 B1 | 2/2004 | Hekal |
| 6,706,946 B1 | 3/2004 | Lankhof et al. |
| 6,709,423 B1 | 3/2004 | Herrlein et al. |
| 6,709,996 B2 | 3/2004 | Mleziva et al. |
| 6,710,223 B1 | 3/2004 | Van Rijswijck et al. |
| 6,710,224 B2 | 3/2004 | Chmielewski et al. |
| 6,712,801 B1 | 3/2004 | Richardson |
| 6,720,471 B1 | 4/2004 | Arndt et al. |
| 6,727,403 B1 | 4/2004 | Ehrnsperger et al. |
| 6,740,184 B2 | 5/2004 | Mortellite et al. |
| 6,746,712 B2 | 6/2004 | Hoffmann et al. |
| 6,752,796 B2 | 6/2004 | Karami |
| 6,756,434 B1 | 6/2004 | Williams et al. |
| 6,761,711 B1 | 7/2004 | Fletcher et al. |
| 6,764,476 B1 | 7/2004 | Ehrnsperger et al. |
| 6,764,479 B2 | 7/2004 | Kusibojoska et al. |
| 6,767,498 B1 | 7/2004 | Talley, Jr. et al. |
| 6,780,958 B2 | 8/2004 | DeGuia |
| 6,786,880 B2 | 9/2004 | Wall |
| 6,786,894 B2 | 9/2004 | Divo et al. |
| 6,790,798 B1 | 9/2004 | Suzuki et al. |
| 6,791,324 B2 | 9/2004 | Maier et al. |
| 6,800,712 B2 | 10/2004 | Doane et al. |
| 6,802,353 B2 | 10/2004 | Malakouti et al. |
| 6,803,496 B2 | 10/2004 | Elder et al. |
| 6,811,239 B1 | 11/2004 | Salacz |
| 6,811,842 B1 | 11/2004 | Ehrnsperger et al. |
| 6,817,992 B1 | 11/2004 | Sassak et al. |
| 6,821,383 B2 | 11/2004 | Shore et al. |
| 6,832,507 B1 | 12/2004 | Van de Haan et al. |
| 6,833,488 B2 | 12/2004 | Bucevshi et al. |
| 6,835,783 B1 | 12/2004 | Gartner et al. |
| 6,838,403 B2 | 1/2005 | Tsai et al. |
| 6,848,140 B2 | 2/2005 | Cho |
| 6,849,067 B2 | 2/2005 | Fletcher et al. |
| 6,854,624 B2 | 2/2005 | Vogt et al. |
| 6,859,966 B2 | 3/2005 | Helmsderfer |
| 6,867,287 B2 | 3/2005 | Carlucci et al. |
| 6,867,343 B2 | 3/2005 | La Fortune |
| 6,888,045 B2 | 5/2005 | Wahlstrom et al. |
| 6,889,397 B2 | 5/2005 | Rosenberg |
| 6,894,085 B2 | 5/2005 | Beaverson et al. |
| 6,905,488 B2 | 6/2005 | Olson |
| 6,905,759 B2 | 6/2005 | Topolkaraev et al. |
| 6,906,131 B2 | 6/2005 | Ahmed et al. |
| 6,906,160 B2 | 6/2005 | Stevens et al. |
| 6,911,024 B2 | 6/2005 | Kusibojoska et al. |
| 6,913,718 B2 | 7/2005 | Ducker et al. |
| 6,914,099 B2 | 7/2005 | Kim |
| 6,916,864 B2 | 7/2005 | Gartner et al. |
| 6,918,900 B2 | 7/2005 | Johnson |
| 6,923,798 B2 | 8/2005 | Heden et al. |
| 6,925,781 B1 | 8/2005 | Knuth et al. |
| 6,925,784 B2 | 8/2005 | Escobar et al. |
| 6,951,591 B2 | 10/2005 | Mortellite et al. |
| 6,953,622 B2 | 10/2005 | Tsai et al. |
| 6,955,668 B2 | 10/2005 | Almberg et al. |
| 6,964,720 B2 | 11/2005 | Schneider et al. |
| 6,971,594 B1 | 12/2005 | Polifka |
| 6,972,010 B2 | 12/2005 | Pesce et al. |
| 6,974,691 B2 | 12/2005 | Fredenburgh et al. |
| 6,983,628 B2 | 1/2006 | Cho |
| 6,984,279 B2 | 1/2006 | Mortell et al. |
| 6,989,193 B2 | 1/2006 | Haile et al. |
| 6,998,512 B2 | 2/2006 | Wahlstrom et al. |
| 7,005,459 B2 | 2/2006 | Hekal |
| 7,008,410 B2 | 3/2006 | Gustin et al. |
| 7,008,685 B2 | 3/2006 | Groitzsch et al. |
| 7,008,887 B2 | 3/2006 | Rearick et al. |
| 7,009,020 B2 | 3/2006 | Doane et al. |
| 7,014,637 B1 | 3/2006 | Denti et al. |
| 7,018,366 B2 | 3/2006 | Easter |
| 7,030,202 B2 | 4/2006 | Gordon, III et al. |
| 7,033,340 B1 | 4/2006 | Muscat et al. |
| 7,037,299 B2 | 5/2006 | Turi et al. |
| 7,047,572 B2 | 5/2006 | Hopkins |
| 7,049,000 B2 | 5/2006 | Fossum et al. |
| 7,052,775 B2 | 5/2006 | Dohrn et al. |
| 7,066,920 B2 | 6/2006 | Mula |
| 7,067,009 B2 | 6/2006 | Bolyard, Jr. et al. |
| 7,067,585 B2 | 6/2006 | Wang et al. |
| 7,069,197 B1 | 6/2006 | Saidane |
| 7,077,924 B2 | 7/2006 | Winkler |
| 7,086,095 B2 | 8/2006 | Faulks |
| 7,096,630 B1 | 8/2006 | Keene et al. |
| 7,105,177 B1 | 9/2006 | Barney et al. |
| 7,111,923 B2 | 9/2006 | Kulpa |
| 7,112,695 B2 | 9/2006 | Eck et al. |
| 7,118,558 B2 | 10/2006 | Wu et al. |
| 7,137,972 B1 | 11/2006 | Holberg |
| 7,147,898 B2 | 12/2006 | Muthiah et al. |
| 7,163,528 B2 | 1/2007 | Christon et al. |
| 7,163,740 B2 | 1/2007 | Rosati et al. |
| 7,166,101 B2 | 1/2007 | Denti et al. |
| 7,175,584 B2 | 2/2007 | Maxton et al. |
| 7,175,616 B2 | 2/2007 | Denti et al. |
| 7,175,910 B2 | 2/2007 | Ehrnsperger et al. |
| 7,176,149 B2 | 2/2007 | Dutkiewicz et al. |
| 7,183,345 B2 | 2/2007 | Kim |
| 7,185,761 B2 | 3/2007 | Molina et al. |
| 7,188,396 B2 | 3/2007 | Melbye et al. |
| 7,198,688 B2 | 4/2007 | Mortell et al. |
| 7,199,203 B2 | 4/2007 | Stevens et al. |
| 7,211,531 B2 | 5/2007 | Schneider et al. |
| 7,220,473 B2 | 5/2007 | Beier et al. |

| | | | | | | |
|---|---|---|---|---|---|---|
| 7,241,280 B2 | 7/2007 | Christon et al. | 7,445,812 B2 | 11/2008 | Schmidt et al. | |
| 7,250,129 B2 | 7/2007 | Williams et al. | 7,456,228 B2 | 11/2008 | Strandburg et al. | |
| 7,252,656 B2 | 8/2007 | Bonelli et al. | 7,458,480 B2 | 12/2008 | Nguyen | |
| 7,260,859 B2 | 8/2007 | Helmsderfer | 7,458,959 B2 | 12/2008 | Fernfors | |
| 7,262,251 B2 | 8/2007 | Kanderski et al. | 7,462,172 B2 | 12/2008 | Wright et al. | |
| 7,270,651 B2 | 9/2007 | Adams et al. | 7,462,755 B2 | 12/2008 | Toro et al. | |
| 7,270,881 B2 | 9/2007 | Schmidt et al. | 7,468,842 B2 | 12/2008 | Steenblik et al. | |
| 7,306,582 B2 | 12/2007 | Adams et al. | 7,470,340 B2 | 12/2008 | Baldauf et al. | |
| 7,311,696 B2 | 12/2007 | Christon et al. | 7,481,222 B2 | 1/2009 | Reissmann | |
| 7,311,941 B2 | 12/2007 | Cesiro et al. | 7,482,058 B2 | 1/2009 | Ahmed et al. | |
| 7,312,268 B2 | 12/2007 | Kim | 7,488,535 B2 | 2/2009 | Ehrnsperger et al. | |
| 7,314,748 B1 | 1/2008 | Fredenburgh et al. | 7,491,862 B1 | 2/2009 | Besemer et al. | |
| 7,326,191 B2 | 2/2008 | Bianco | 7,500,339 B2 | 3/2009 | Knuth et al. | |
| 7,328,568 B2 | 2/2008 | Rahn | 7,500,941 B2 | 3/2009 | Coe et al. | |
| 7,333,268 B2 | 2/2008 | Steenblik et al. | 7,507,459 B2 | 3/2009 | Turner et al. | |
| 7,344,775 B2 | 3/2008 | Stevens et al. | 7,513,197 B2 | 4/2009 | Kuckelmann et al. | |
| 7,347,848 B2 | 3/2008 | Fernfors | 7,517,586 B2 | 4/2009 | Fossum et al. | |
| 7,350,663 B2 | 4/2008 | Chomik | 7,521,109 B2 | 4/2009 | Suzuki et al. | |
| 7,361,246 B2 | 4/2008 | Chang et al. | 7,524,561 B2 | 4/2009 | Schmidt et al. | |
| 7,361,694 B2 | 4/2008 | Strandburg et al. | 7,527,823 B2 | 5/2009 | Tombult-Meyer et al. | |
| 7,364,687 B2 | 4/2008 | Maschino et al. | 7,527,848 B2 | 5/2009 | Baldauf | |
| 7,365,190 B2 | 4/2008 | Couture et al. | 7,533,709 B2 | 5/2009 | Meyer | |
| 7,377,203 B2 | 5/2008 | Chomik | 7,534,237 B2 | 5/2009 | Olson et al. | |
| 7,395,646 B2 | 7/2008 | Salman et al. | 7,537,585 B2 | 5/2009 | Christon et al. | |
| 7,396,585 B2 | 7/2008 | Schmidt et al. | 7,541,395 B2 | 6/2009 | Reimann et al. | |
| 7,402,157 B2 | 7/2008 | Christon et al. | 7,541,398 B2 | 6/2009 | Sun et al. | |
| 7,402,339 B2 | 7/2008 | Schmidt et al. | 7,552,572 B2 | 6/2009 | Bois | |
| 7,404,810 B2 | 7/2008 | Toro et al. | 7,553,532 B2 | 6/2009 | Turner et al. | |
| 7,405,341 B2 | 7/2008 | Beruda et al. | D596,287 S | 7/2009 | Tan | |
| 7,406,814 B2 | 8/2008 | Morand | 7,569,038 B2 | 8/2009 | Salem, Jr. | |
| 7,423,090 B2 | 9/2008 | Doane et al. | 7,581,514 B2 | 9/2009 | Bonfoey | |
| 7,423,106 B2 | 9/2008 | Doane et al. | 7,585,169 B2 | 9/2009 | Jahn et al. | |
| 7,426,765 B2 | 9/2008 | Helmsderfer | 7,589,249 B2 | 9/2009 | Gubernick et al. | |
| 7,427,437 B2 | 9/2008 | Schmidt et al. | 7,615,038 B2 | 11/2009 | Kropf | |
| 7,431,715 B2 | 10/2008 | Guidotti et al. | 2003/0065301 A1 | 4/2003 | Elliott | |
| 7,434,410 B2 | 10/2008 | Ford | 2006/0282056 A1* | 12/2006 | McDonald | 604/385.13 |
| 7,439,276 B2 | 10/2008 | Srandburg et al. | 2008/0114320 A1* | 5/2008 | Beck et al. | 604/385.01 |
| 7,442,332 B2 | 10/2008 | Cancio et al. | | | | |

\* cited by examiner

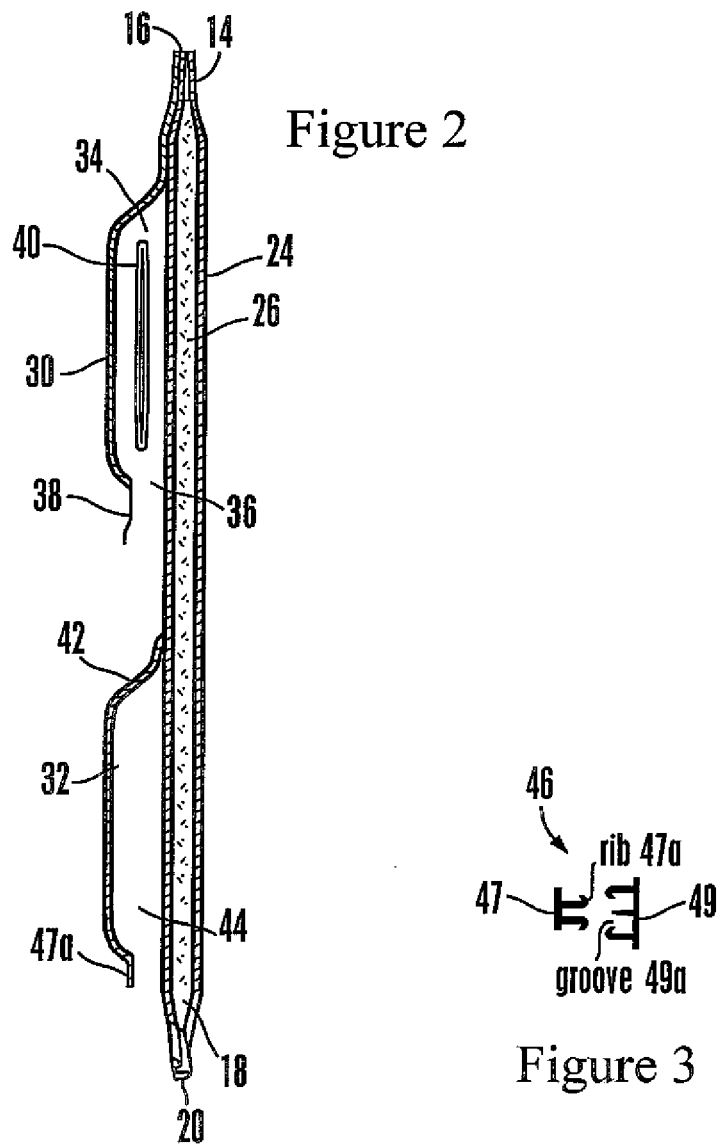
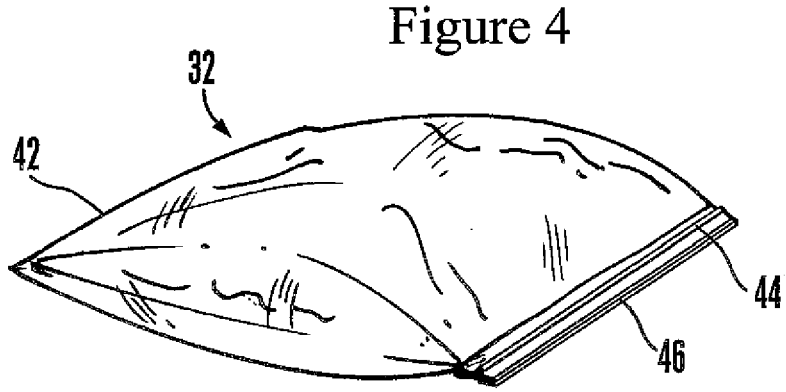

DISPOSABLE DIAPER WITH POUCHES

The present invention relates generally to disposable baby diapers with pouches.

BACKGROUND OF THE INVENTION

Disposable diapers are convenient because they do not require washing and are easy to put on a baby. As understood herein, however, two chores remain once a child soils a disposable diaper, namely, gently cleaning the child and doing something with the soiled diaper until it can be discarded into an appropriate trash receptacle.

SUMMARY OF THE INVENTION

Accordingly, a disposable diaper includes a diaper body that defines an inner surface configured for placement against a baby, an outer surface opposite the inner surface, a front portion configured for placement over a baby's abdomen, a rear portion configured for placement over a baby's backside, and a crotch portion therebetween. A first closable pouch is formed on the outer surface of the front portion. The first closable pouch defines an open end, a closed end opposite the open end, and a closure member for selectively closing the open end. A second closable pouch is formed on the outer surface of the rear portion. The second closable pouch defines an open end, a closed end opposite the open end, and a closure member for selectively closing the opening. One of the pouches establishes an invertable pouch so that the diaper body can be urged against the closed end of the invertable pouch to advance the closed end thereof through the open end and thereby invert the pouch inside out with the diaper body substantially enclosed in the invertable pouch. Then, the closure member of the invertable pouch can be manipulated to close the open end of the pouch with the diaper body inside the invertable pouch.

In some embodiments the closure member of invertable pouch may include a closure element disposed on an outer surface of the pouch before inversion of the pouch such that the closure element is disposed inside the invertable pouch after inversion. The closure element can be a rib or a groove and the closure member of the invertable pouch can include a second closure element opposite the first closure element. The second closure element is a rib if the first closure element is a groove and a groove if the first closure element is a rib.

In example non-limiting embodiments the second pouch is the invertable pouch and the first pouch holds a wet wipe. The closure member of the first pouch may include adhesive tape.

In some implementations the front portion of the diaper body defines a top edge and the closed end of the first pouch is between the top edge and the open end of the first pouch. On the other hand, the rear portion of the diaper body defines a bottom edge and the open end of the second pouch is between the bottom edge and the closed end of the second pouch. The top and bottom edges of the diaper body can be held together along end segments thereof by tape closures when the diaper is on a baby to hold the diaper on the baby.

In another aspect, a disposable diaper has a wet wipe pouch with a wet wipe inside and a soil pouch with a closable open end, such that when the diaper has been soiled the wet wipe can be removed from the wet wipe pouch and used to clean a baby and then the diaper, once removed from the baby, can be inverted into the soil pouch, which inverts inside out with a soiled part of the diaper inside. A closure is provided to close the open end of the soil pouch after inversion to contain the soiled part of the diaper inside the soil pouch.

In another aspect, a method associated with removing a diaper body from a wearer includes, with the diaper body removed from the wearer, urging the diaper body against an end of a pouch coupled to the diaper body to invert the pouch with the diaper inside the pouch. The method also includes manipulating a closure to close the pouch with the diaper inside the pouch.

The details of the present invention, both as to its structure and operation, can best be understood in reference to the accompanying drawings, in which like reference numerals refer to like parts, and in which:

BRIEF DESCRIPTION OF THE DRAWINGS

FIG. 2 is a side view of the diaper as seen along the line 2-2 in FIG. 1;

FIG. 3 is a detail of the rib and groove of an example closure; and

FIG. 4 is a perspective view of the soil pouch containing the diaper after inversion.

DETAILED DESCRIPTION OF THE PREFERRED EMBODIMENT

Figure 1:
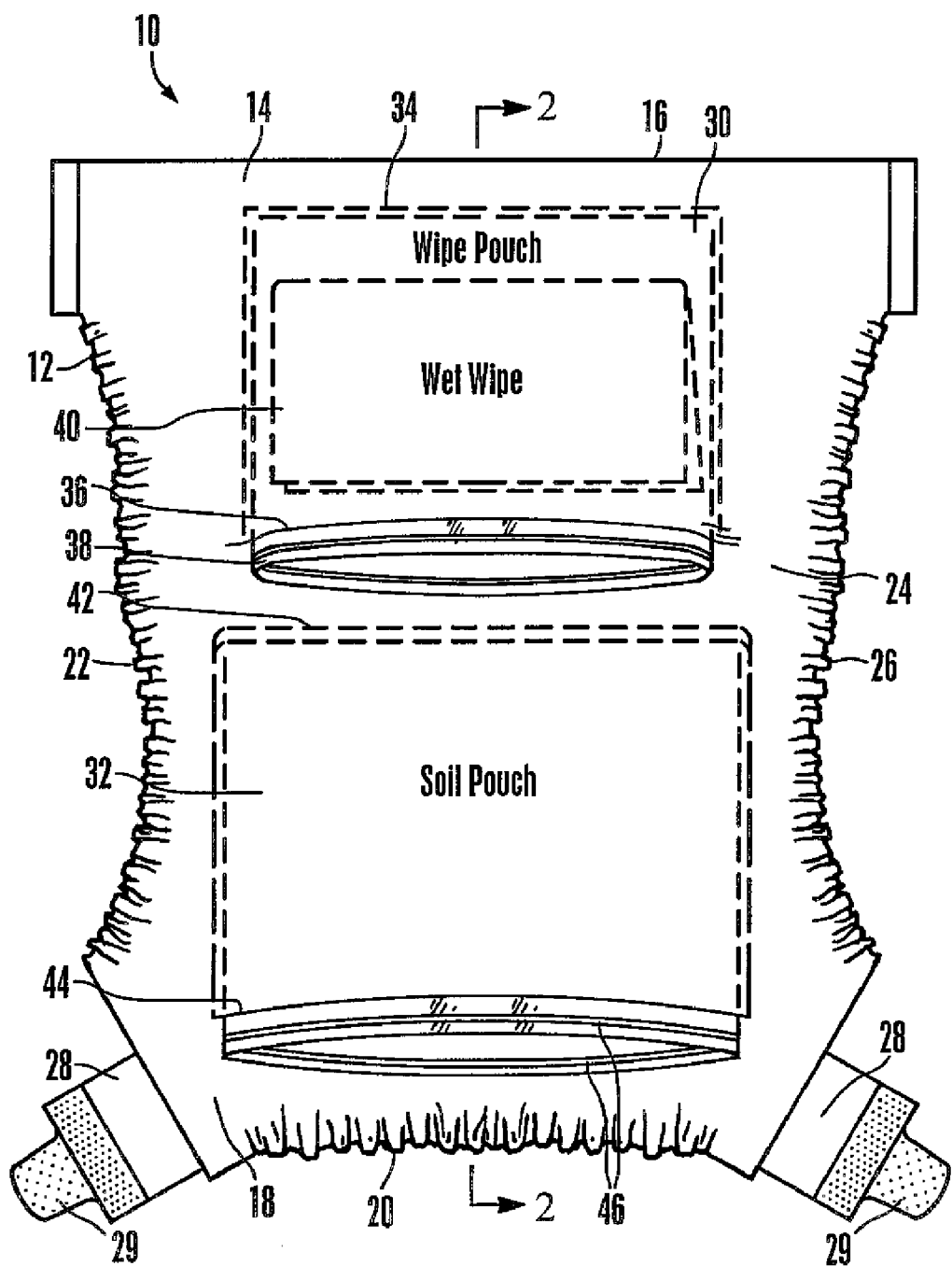
FIG. 1 is a perspective view of an example diaper laid out in a flat configuration with the outside of the diaper facing the viewer, showing the wet wipe in phantom.

Referring initially to FIGS. 1 and 2, a disposable diaper is shown, generally designated 10, which includes a diaper body 12. The diaper body 12 has a front portion 14 configured for placement over a baby's abdomen. The front portion 14 terminates in a horizontal top edge 16. The diaper body 12 also has a rear portion 18 configured for placement over a baby's backside and defining a bottom edge 20 parallel to the top edge 16. As shown in FIG. 1, the front and rear portions 14, 18 taper inwardly to a crotch portion 22. The diaper body 12 typically is unitary and the outside surface 24 (i.e., the surface facing away from the baby) typically is not absorbent, as opposed to the inside surface 26 (the surface positioned against the baby), which typically is absorbent to water.

Also, to hold the diaper body 12 onto the baby, the rear portion 18 may define transversely opposed tape wings 28 each bearing adhesive tape 29 that can engage the outer surface of the front portion 14 near the top edge 16 to hold the outer segments of the edges 16, together.

At least one and preferably two pouches are on the diaper. The pouches discussed below may be made integrally with the diaper body 12 or established by thin, typically flexible plastic sheets three edges of which are adhesively bonded to the diaper body or are otherwise attached thereto, e.g., by ultrasonic or rf bonding methods.

With greater specificity, a wet wipe pouch 30 can be on the outer surface of the front portion 14 as shown while a soil pouch 32 is on the outer surface of the rear portion 18, it being understood that the positions of the pouches on the diaper body portions may be reversed. As shown, the wet wipe pouch 30 has three enclosed sides including a closed end 34 that faces the top edge 16 of the front portion 14 of the diaper. Opposite the closed end 34 is an open end or side 36 that can be selectively closed by a closure member 38 such as adhesive tape. Accordingly, a wet wipe 40 or other cleansing implement may be enclosed in the wet wipe pouch 30, the closure member 38 manipulated to close the open end or side 36, and then manipulated again to permit access to the interior of the pouch so that the wet wipe 40 may be removed and used to clean a baby.

Likewise, the soil pouch 32 has three closed sides including a closed end or side 42 and an opposed open end 44 which may be selectively closed by a closure member 46. The closure member 46 may be adhesive tape or may be other structure such as a rib-and-groove arrangement. In any case, the open end 44 in the example embodiment shown may be closer to the bottom edge 20 than is the closed end 42 of the soil pouch 32.

Furthermore, the closure member 46 is operably disposed near the edge of the open end 44 as shown preferably on the outside surface of the pouch 32 as shown in FIG. 2. It will readily be appreciated that when the soil pouch 32 is inverted inside-out as described below, the closure member 46 is conveniently disposed on what will then be the inner-facing part of the soil pouch 32 to facilitate closing the open end 44 as shown in FIG. 3. Thus, for example and as shown in FIG. 3, when the closure member 46 includes a first generally linear closure element 47 having two resilient ribs 47a that are lockably received in corresponding grooves 49a of a second generally linear closure element 49, the elements 47, 49 are separated from each other by pouch material when the diaper is not inverted and so cannot be engaged with each other. However, upon pouch inversion as shown in FIG. 3 the elements 47, 49 face each other and thus can be engaged with each other to hold the pouch closed. It is to be understood that one of the elements 47, 49 may be on the diaper body and the other may be on the soil pouch 32.

With the above structure in mind, use of the diaper 10 can now be appreciated. The diaper 10 may be vended with the wet wipe 40 in the wet wipe pouch 30, or a buyer may be instructed to place a wet wipe in the pouch for future use. In any case, the diaper is placed on a baby and the closure tape 29 fastened to hold the ends of the edges 16, 20 together to keep the diaper on the baby.

When the baby soils the tape 29 is unfastened and the diaper removed from the baby. If desired the wet wipe pouch closure 38 is manipulated to open the wet wipe pouch 30 and extract the wet wipe 40 therefrom, for use in cleaning the baby. The used wet wipe 40 may then be placed on the diaper body 12.

The diaper body 12 is then folded or rolled or otherwise urged against the closed end 42 of the soil pouch 32 to push the closed end 42 through the open end 44, inverting the soil pouch inside out as shown in FIG. 4. This results in the diaper body 12 being disposed within the inverted soil pouch 32. The soil pouch closure member 46 is then manipulated to close the open end 44 of the pouch with the soiled diaper body inside. The diaper 10 in its inverted, closed-off configuration may then be disposed of at the leisure of the parent.

In some embodiments only one pouch need be provided, e.g., the soil pouch, with the wet wipe being disposed in the soil pouch at vending, removed for cleaning, and then placed back into the soil pouch prior to inverting the diaper into the soil pouch.

While the particular DISPOSABLE DIAPER WITH POUCHES is herein shown and described in detail, it is to be understood that the subject matter which is encompassed by the present invention is limited only by the claims.

What is claimed is:

1. A disposable diaper comprising:
   a diaper body defining an inner surface configured for placement against a baby, an outer surface opposite the inner surface, a front portion configured for placement over a baby's abdomen, a rear portion configured for placement over a baby's backside, and a crotch portion therebetween;
   a first closable pouch formed on the outer surface of the front portion, the first closable pouch defining an open end, a closed end opposite the open end, and a closure member for selectively closing the open end; and
   a second closable pouch formed on the outer surface of the rear portion, the second closable pouch defining an open end, a closed end opposite the open end, and a closure member for selectively closing the opening, one of the pouches establishing an invertable pouch, the closed end of the second pouch being juxtaposed with the open end of the first pouch such that the oven end of the second pouch is distanced from the open end of the first pouch by the second pouch;
   wherein the diaper body can be urged against the closed end of the invertable pouch to advance the closed end thereof through the open end and thereby invert the pouch inside out with the diaper body substantially enclosed in the invertable pouch, such that the closure member of the invertable pouch can be manipulated to close the open end of the pouch with the diaper body inside the invertable pouch.

2. The diaper of claim 1, wherein the closure member of invertable pouch includes a closure element disposed on an outer surface of the pouch before inversion of the pouch such that the closure element is disposed inside the invertable pouch after inversion.

3. The diaper of claim 2, wherein the closure element is a first closure element selected from the group of: a rib, a groove, and the closure member of the invertable pouch comprises a second closure element opposite the first closure element, the second closure element being a rib if the first closure element is a groove and the second closure element being a groove if the first closure element is a rib.

4. The diaper of claim 1, wherein the second pouch is the invertable pouch and the first pouch holds a wet wipe.

5. The diaper of claim 4, wherein the closure member of the first pouch includes adhesive tape.

6. The diaper of claim 1, wherein the front portion of the diaper body defines a top edge and the closed end of the first pouch is between the top edge and the open end of the first pouch.

7. The diaper of claim 1, wherein the rear portion of the diaper body defines a bottom edge and the open end of the second pouch is between the bottom edge and the closed end of the second pouch, the top and bottom edges being holdable together along end segments thereof by tape closures when the diaper is on a baby to hold the diaper on the baby.

8. A disposable diaper comprising:
   at least a soil pouch with a closable open end, such that when the diaper has been soiled the diaper, once removed from the baby, can be inverted into the soil pouch, which inverts inside out with a soiled part of the diaper inside;
   a closure to close the open end of the soil pouch after inversion to contain the soiled part of the diaper inside the soil pouch;
   a diaper body defining an inner surface configured for placement against a baby, an outer surface opposite the inner surface, a front portion configured for placement over a baby's abdomen, a rear portion configured for placement over a baby's backside, and a crotch portion therebetween;
   a wet wipe pouch on the diaper body and being provided with a wet wipe inside;
   wherein the wet wipe can be removed from the wet wipe pouch and used to clean a baby, the wet wipe pouch defining a closed end and an open end, the soil pouch defining an open end and a closed end, the open ends of the pouches being separated from each other by a body of one of the pouches.

9. The diaper of claim 8, wherein the closure of the soil pouch includes a closure element disposed on an outer surface of the soil pouch before inversion of the soil pouch such that the closure element is disposed inside the soil pouch after inversion.

10. The diaper of claim 9, wherein the closure element is a first closure element selected from the group of: a rib, a groove, and the closure of the soil pouch comprises a second closure element opposite the first closure element, the second closure element being a rib if the first closure element is a groove and the second closure element being a groove if the first closure element is a rib.

11. The diaper of claim 8, wherein the wet wipe pouch is associated with a closure member.

12. The diaper of claim 11, wherein the closure member includes adhesive tape.

13. The diaper of claim 8, wherein the front portion of the diaper body defines a top edge and a closed end of the wet wipe pouch is between the top edge and an open end of the wet wipe pouch.

14. The diaper of claim 8, wherein the rear portion of the diaper body defines a bottom edge and the open end of the soil pouch is between the bottom edge and a closed end of the soil pouch, the top and bottom edges being holdable together along end segments thereof by tape closures when the diaper is on a baby to hold the diaper on the baby.

* * * * *